United States Patent [19]

Brophy et al.

[11] Patent Number: 4,705,906

[45] Date of Patent: Nov. 10, 1987

[54] SELECTIVE HYDROGENATION OF ACETYLENE

[75] Inventors: John H. Brophy, Camberley; Anthony Nock, Sandhurst, both of England

[73] Assignee: The British Petroleum Company, p.l.c., London, England

[21] Appl. No.: 930,003

[22] Filed: Nov. 12, 1986

[30] Foreign Application Priority Data

Nov. 27, 1985 [GB] United Kingdom ................. 8529245

[51] Int. Cl.$^1$ ............................................. C07C 5/05
[52] U.S. Cl. ..................................... 585/262; 585/260; 585/271; 585/275; 585/273; 585/277
[58] Field of Search ............... 585/262, 258, 259, 260, 585/261, 271, 273, 274, 275, 276, 277; 502/307

[56] References Cited

U.S. PATENT DOCUMENTS

| | | | |
|---|---|---|---|
| 3,308,180 | 3/1967 | Fleming | 585/251 |
| 3,444,256 | 5/1969 | Engelhard et al. | 585/262 |
| 3,444,257 | 5/1969 | Engelhard et al. | 585/262 |
| 3,634,536 | 1/1972 | Fravel et al. | 585/262 |
| 3,662,015 | 5/1972 | Komatsu et al. | 585/261 |
| 3,674,886 | 7/1972 | Komatsu et al. | 585/261 |
| 4,059,504 | 11/1977 | Bauer | 585/261 |
| 4,251,674 | 2/1981 | Callejas et al. | 585/259 |
| 4,517,395 | 5/1985 | Obenaus et al. | 585/260 |

FOREIGN PATENT DOCUMENTS

| | | |
|---|---|---|
| 0070690 | 1/1983 | European Pat. Off. . |
| 0178853 | 6/1986 | European Pat. Off. . |
| 989302 | 4/1965 | United Kingdom ................. 585/262 |

Primary Examiner—Asok Pal
Attorney, Agent, or Firm—Brooks, Haidt, Haffner & Delahunty

[57] ABSTRACT

Ethylene is produced by the selective hydrogenation of acetylene in the presence of carbon monoxide at a concentration of greater than 1% vol, generally greater than 5% vol, and optionally also ethylene by contact at an elevated temperature in the range from 100° to 500° C. with a catalyst comprising a metal oxide or sulphide or mixture of metal oxides or sulphides having hydrogenation activity, for example ZnO either alone or in combination with other metal oxides or sulphides.

12 Claims, No Drawings

SELECTIVE HYDROGENATION OF ACETYLENE

The present invention relates in general to a process for the selective hydrogenation of acetylene to produce ethylene and in particular to a process for the selective hydrogenation of acetylene in the presence of carbon monoxide and, optionally also, ethylene to produce ethylene.

The selective hydrogenation of acetylene in the presence of olefinic hydrocarbons has long been the subject of study in connection with petrochemical processes, such as the steam cracking of naphtha, where the selective removal of acetylene in an ethylene-rich cut is mandatory to meet the ethylene specifications. Catalysts for the selective hydrogenation of acetylene in the presence of ethylene are typically supported metals of Group VIII of the Periodic Table, of which palladium was shown to be the most active and selective metal for the hydrogenation of acetylenics to the corresponding olefins. Nevertheless, the use of palladium is not without its problems. Thus, whilst palladium catalysts are reasonably tolerant of the usual organic impurities which act solely as activity moderators, they are poisoned by, for example COS and $H_2S$ at low temperature. In particular, they are poisoned at low temperatures by high concentrations of carbon monoxide, such as those associated with unsaturated hydrocarbon-containing products obtained by the partial combustion of gaseous paraffinic hydrocarbons. This is to be contrasted with their behaviour at low carbon monoxide concentrations, typically at concentrations less than 1% vol, at which moderation of catalytic activity is reported to enhance the selectivity of acetylene hydrogenation to ethylene. The process of the present invention is not concerned with carbon monoxide levels at which selectivity enhancement is observed with noble metal catalysts. The carbon monoxide concentrations with which the present invention is concerned are greater than 1% vol, generally greater than 5% vol.

Although the palladium catalysts are active at high temperatures even in the presence of carbon monoxide, the selectivity of acetylene hydrogenation to ethylene is drastically reduced by simultaneous hydrogenation of ethylene to ethane.

We have now found catalysts which are active for the selective hydrogenation of acetylene to ethylene in the presence of carbon monoxide and, optionally also, ethylene.

Accordingly the present invention provides a process for the production of ethylene by the selective hydrogenation of acetylene to ethylene in the presence of carbon monoxide at a concentration of greater than 1% vol and optionally also ethylene, which process comprises contacting a feedstock comprising carbon monoxide, hydrogen, acetylene and, optionally also ethylene, at an elevated temperature in the range from 100° to 500° C. with a catalyst comprising a metal oxide or sulphide or mixture of metal oxides or sulphides having hydrogenation activity.

Suitable metal oxides or sulphides which may be used as catalysts in the process of the present invention include, for example oxides or sulphides of zinc, copper, gallium, cadmium, chromium, molybdenum, tungsten, cobalt, nickel, ruthenium and iron, and mixtures of two or more thereof. A preferred catalyst is zinc oxide or sulphide, either alone or in combination with at least one other metal oxide or sulphide, for example chromium, thorium or gallium oxide or sulphide. Examples of suitable catalysts include zinc(II)oxide(ZnO), zinc(II)oxide(ZnO)/ chromium(III)oxide($Cr_2O_3$) and Zn(II)oxide(ZnO)/thorium(IV)oxide ($ThO_2$)/gallium(III)oxide($Ga_2O_3$). A preferred catalyst is zinc(II)oxide(ZnO). Catalysts of the zinc oxide/thorium oxide/gallium oxide-type are described in our European application publication No. 0070690, to which the reader is referred for further details. Suitably in the $Cr_2O_3$/ZnO catalyst the molar ratio of $Cr_2O_3$ to ZnO may be in the range from 5:1 to 1:5, preferably from 1:1 to 1:3. The more acidic of the metal oxides may also, in addition to performing the selective hydrogenation reaction, produce oligomers in the form for example of higher olefins, which may reduce the overall selectivity of the process to ethylene, but nevertheless are valuable and desirable by-products.

Catalysts may suitably be prepared by mixing the individual oxides, or compounds thermally decomposable to the oxides, for example by mixing a suspension of the compounds in water and evaporating the mixture to form a cake. Precipitation or coprecipitation may also be employed. The cake may thereafter be filtered, washed and dried and the dried cake crushed and calcined at elevated temperature to produce the desired catalyst composition. The calcination may suitably be carried out in an oxidising atmosphere, for example in air.

The catalysts may, if desired, be subjected to a suitable pretreatment. The pretreatment may take the form of heating in air at elevated temperature or heating in nitrogen or hydrogen or incorporating an effective amount of an alkali metal, for example potassium, or a combination thereof.

The feedstock comprising carbon monoxide, hydrogen, acetylene and, optionally also, ethylene may be obtained from any convenient source. Thus, the components may be derived individually and mixed in the presence of the catalyst or they may be co-produced and the co-product contacted with the catalyst. It is preferred to co-produce the components of the feedstock, suitably by partially oxidising a gaseous paraffinic hydrocarbon under conditions whereby simultaneous cracking of the hydrocarbon is achieved.

Suitable gaseous paraffinic hydrocarbons include methane, ethane and propane. A mixture of hydrocarbons, such as for example natural gas, is a particularly suitable feed to the partial oxidation process.

In a preferred embodiment, a feedstock mixture comprising acetylene, ethylene, carbon monoxide and hydrogen is produced by the process described in our copending European application publication No. 0163385 (BP Case No. 5791) to which the reader is referred for further details.

In a particularly preferred embodiment of the present invention a feedstock mixture comprising acetylene, ethylene, carbon monoxide and hydrogen is produced by the process described in our copending European application publication No. 0178853 (BP Case No. 5959) to which the reader is referred for further details.

In a further embodiment a feedstock mixture comprising acetylene, ethylene, carbon monoxide and hydrogen is produced by the conversion process described in our copending International application No. PCT/GB86/00198 (Case No. 6042), reference to which may be made for further details.

Flame or partial combustion processes for the production of acetylene from hydrocarbons, for example the BASF Process, the SBA (Société Belge de l'Azote et des Produits Chimiques de Marly) Process, the Montecatini Process, the Hoechst HTP (high temperature pyrolysis) Process and the BASF Submerged-Flame Process. Although those skilled in the art will be conversant with the foregoing processes, further details of the processes may be found in standard reference works; for example Kirk Othmer's 'Encyclopaedia of Chemical Technology'. The products of the aforesaid processes comprising acetylene, ethylene, carbon monoxide and hydrogen are suitable for use as feedstocks in the selective hydrogenation process of the present invention.

The concentrations of carbon monoxide in the products of the aforesaid partial oxidation processes will depend upon a number of factors, including the nature of the feed, the nature of the oxidant and the presence or absence of hydrogen. Typically, using a methane/oxygen feed to the partial oxidation the carbon monoxide concentration in the product gases will be ca 25% vol on a dry gas basis (ca 15% on a wet gas basis), using methane/air feed the carbon monoxide concentration will be ca 20% vol on a dry gas basis (ca 10% vol on a wet gas basis) and using a methane/hydrogen/oxygen feed the carbon monoxide concentration will be ca 10% vol on a dry gas basis (ca 5% vol wet gas basis). Generally, therefore, the carbon monoxide concentration may suitably be in the range from 5 to 45% vol, preferably from 5 to 35% vol, though the process may be operated at higher carbon monoxide concentrations if desired. The Partial oxidation of ethane will typically produce lower concentrations of carbon monoxide in the product gas and higher concentrations of ethylene.

The product of the aforesaid processes may be used as feedstock in the process of the present invention without any intervening steps, other than adjustment of its temperature and pressure if necessary, or, if desired, components may be removed. For example, minor amounts of carbon dioxide and water may be removed from the product. It is preferred, however, to use the product as feedstock to the process of the present invention without any intervening separation steps.

The selective hydrogenation of acetylene according to the present invention is operated at a temperature in the range from 100° to 500° C., generally greater than 250° C. The optimum temperature will depend on the nature of the catalyst selected and the operating conditions, for example the GHSV and partial pressure of hydrogen. The pressure may suitably be in the range from 1 to 50 bars. The GHSV may suitably be in the range from 100 to 10,000 $h^{-1}$.

Whilst it is preferred to operate the process of the invention by contacting a gaseous feedstock with the hydrogenation catalyst in the form of a fixed bed, a moving bed or a fluidised bed, it may be operated in other ways, for example by contacting a gaseous feedstock with a slurry of the catalyst in a suitable solvent.

The process may be operated batchwise or continuously, preferably continuously.

The invention will now be further illustrated by reference to the following Examples.

The catalysts used in Comparison Tests 1-4 and Examples 1-4 were prepared as follows:

ZnO

A 1M $NH_4HCO_3$ solution was added dropwise, at room temperature to a solution of $Zn(NO_3)_2.6H_2O$ (90.2 g) in 700 ml distilled water with rapid stirring until a pH=6.0 was obtained. The precipitate was filtered, washed and then dried in an oven at 100° C. for 16 h. The oxide was obtained by calcination of the solid at 400° C. for 4h. The catalyst was pretreated in situ by heating in air at 400° C. for 3h.

$Cr_2O_3$—ZnO

A solution of $CrCl_3.6H_2O$ (53.3 g) in 500 ml distilled water was added to $Zn(NO_3)_2.6H_2O$ (59.5 g) in 500 ml distilled water. The metal hydroxides were precipitated by dropwise addition of a 25% ammonia solution at room temperature with stirring to give a pH=6.2. The precipitate was filtered, washed with distilled water and then dried in an oven at 100° C. for 16h. Finally, the solid was calcined at 500° C. for 3h to give the mixed metal oxide catalyst.

The metal ion molar ratio was 1:1, i.e. 1:2 (mol) $Cr_2O_3$:ZnO.

The catalyst was pretreated in situ by heating in air at 400° C. for 3h.

$ThO_2/ZnO/Ga_2O_3$ $Th(NO_3)_4.6H_2O$ (77.9 g) and $Zn(NO_3)_2.6H_2O$ (45.1 g.) were mixed with 525 ml gallium solution (0.025 g/ml in $HNO_3$, adjusted to pH 2.7 with $NH_3$) and $H_2O$ (700 ml). 1M $NH_4HCO_3$ was added to pH 6.0 with rapid stirring. The mixture was filtered, washed, dried and then calcined at 400° C. for 4h.

The metal ion molar ratio was 0.7 (Th):0.8(Zn):1.0(Ga) corresponding to a $ThO_2$:ZnO:$Ga_2O_3$ molar ratio of 1.4:1.6:1.0.

The catalyst was pretreated in situ by heating at 400° C. in air for 3h and then at 225° C. in hydrogen for 16h.

$Pd/Al_2O_3$

A commercially available GIRDLER G63 catalyst was employed.

It was pretreated in situ by heating in nitrogen at 400° C. for 2h.

Comparison Test 1

A gaseous feed consisting of acetylene (6.4% by volume), ethylene (3.2% by volume), carbon monoxide (29% by volume) and hydrogen (61.4% by volume) was contacted in a reactor consisting of a ½" stainless steel tube fitted with a ⅛" central thermocouple well at a GHSV of 870$h^{-1}$ with a commercially available palladium supported on alumina catalyst (held in position using quartz wool and antibumping granules) maintained at a temperature of 115° C. (the recommended operating temperature) operated at 1 bar pressure for a period of 1 hour.

The conditions and results obtained are given in Table 1.

Comparison Test 2

Comparison Test 1 was repeated except that the feed was contacted with the catalyst for a period of 2 hours.

The conditions and results obtained are given in Table 1.

Comparison Tests 1 and 2 are not examples according to the present invention and are included to show that the conventional acetylene hydrogenation catalyst is rapidly poisoned by carbon monoxide in the feed at low temperatures.

Comparison Test 3

Comparison Test 2 was repeated except that the temperature was raised to 177° C., the GHSV reduced to 293 $h^{-1}$ and the pressure raised to 3 bar.

The conditions and results obtained are given in Table 1.

Comparison Test 4

Comparison Test 3 was repeated except that the temperature was raised to 377° C. and the GHSV was increased to 1010 $h^{-1}$.

The conditions and results obtained are given in Table 1.

Comparison Tests 3 and 4 are not examples according to the invention and are included for the purpose of demonstrating that at elevated temperature the conventional acetylene hydrogenation catalyst is very active for hydrogenation, but is unselective, the acetylene being totally hydrogenated to ethane.

EXAMPLE 1

Comparison Test 4 was repeated except that a $ThO_2/ZnO/Ga_2O_3$ catalyst was employed and the GHSV was decreased to 1000 $h^{-1}$.

The conditions and results obtained are given in Table 1.

The results demonstrate that a $ThO_2/ZnO/Ga_2O_3$ catalyst is very active for the selective hydrogenation of acetylene to ethylene in the presence of carbon monoxide and ethylene. Moreover, the catalyst also produces valuable oligomers (31% selectivity) which include higher olefins, propene, butenes (10%) and $C_5^+$ aliphatics and aromatics.

Comparison Test 5

Example 1 was repeated except that the temperature was reduced to 115° C. The catalyst was inactive with respect to the process of the present invention.

This is not an example according to the invention and is included to show that the $ThO_2/ZnO/Ga_2O_3$ catalyst is inactive with respect to the process of the present invention at temperatures normally employed for the conventional palladium catalyst.

EXAMPLE 2

Example 1 was repeated except that instead of the $ThO_2/ZnO/Ga_2O_3$ catalyst there was used a $Cr_2O_3/ZnO$ catalyst.

EXAMPLE 3

Example 1 was repeated except that instead of the $ThO_2/ZnO/Ga_2O_3$ catalyst there was used a ZnO catalyst and the GHSV was reduced to 985 $h^{-1}$.

EXAMPLE 4

Example 3 was repeated except that the temperature was reduced to 327° C. and the GHSV was increased to 1465 $h^{-1}$.

The conditions and results obtained for Examples 2 to 4 are given in Table 1.

The results demonstrate that both $Cr_2O_3/ZnO$ and ZnO alone are very active catalysts for the selective hydrogenation of acetylene in the presence of carbon monoxide and ethylene.

TABLE 1

|  | Comparative Tests | | | | Example 1 | Example 2 | Example 3 | Example 4 |
| --- | --- | --- | --- | --- | --- | --- | --- | --- |
|  | 1 | 2 | 3 | 4 | | | | |
| Catalyst | $Pd/Al_2O_3$ (C63) | | | | $ThO_2/ZnO/Ga_2O_3$ | $Cr_2O_3/ZnO$ | ZnO | ZnO |
| GHSV/$h^{-1}$ | 870 | 870 | 293 | 1010 | 1000 | 1000 | 985 | 1465 |
| Temp/°C. | 115 | 115 | 177 | 377 | 377 | 377 | 377 | 327 |
| Pressure/bar | 1 | 1 | 3 | 3 | 3 | 3 | 3 | 3 |
| Hours-on-Stream | 1 | 2 | 2 | 2 | 2 | 2 | 2 | 2 |
| $C_2H_2$ Conversion | 57 | 17 | 100 | 100 | 100 | 100 | 100 | 100 |
| Selectivities % C-mol | | | | | | | | |
| $CO_2$ | — | — | — | 3 | 9 | 1 | 1 | — |
| $CH_4$ | — | — | — | 17 | 1 | 2 | 1 | 1 |
| $C_2H_4$ | 91 | 78 | — | — | 56 | 56 | 79 | 71 |
| $C_2H_6$ | — | 7 | 95 | 73 | 3 | 6 | 3 | 2 |
| $C_3^+$ | 9 | 15 | 5 | 7 | 31 | 35 | 16 | 26 |

Feed Composition (% vol)
$C_2H_2$ = 6.4%
$C_2H_4$ = 3.2%
CO = 29%
$H_2$ = 61.4%

We claim:

1. A process for the production of ethylene by the selective hydrogenation of acetylene to ethylene in the presence of carbon monoxide at a concentration of greater than 1% by vol of the total feed, which process comprises contacting a feedstock comprising carbon monoxide, hydrogen, and acetylene, at an elevated temperature in the range from 100° to 500° C. with a catalyst,
   wherein the catalyst is zinc oxide or sulphide, either alone or in combination with at least one other metal oxide or sulphide.

2. A process according to claim 1 wherein the metal oxide or sulphide having hydrogenation activity is an oxide or sulphide of either zinc, gallium, copper, cadmium, chromium, molybdenum, tungsten, cobalt, nickel, ruthenium or iron, or a mixture of two or more thereof.

3. A process according to claim 1 wherein the catalyst is zinc(II)oxide.

4. A process according to claim 1 wherein the catalyst is either zinc(II)oxide/chromium(III)oxide or zinc(II)oxide/thorium(IV)oxide/gallium(III)oxide.

5. A process according to claim 1 wherein the catalyst is pretreated either by heating in air, nitrogen or by incorporating an effective amount of an alkali metal or by a combination thereof.

6. A process according to claim 1 wherein the feedstock is obtained by partially oxidising a gaseous paraffinic hydrocarbon under conditions whereby simultaneous cracking of the hydrocarbon is achieved.

7. A process according to claim 1 wherein the temperature is greater than 250° C.

8. A process according to claim 1 wherein the pressure is in the range from 1 to 50 bars.

9. A process according to claim 1 wherein the GHSV is in the range from 100 to 10,000 $h^{-1}$.

10. A process according to claim 1, wherein the feedstock further comprises ethylene.

11. A process according to claim 1, wherein the carbon monoxide concentration is greater than 5% by volume of the total feed.

12. A process according to claim 1, wherein the carbon monoxide concentration is from 5% to 45% by volume of the total feed.

* * * * *

UNITED STATES PATENT AND TRADEMARK OFFICE
CERTIFICATE OF CORRECTION

PATENT NO. : 4,705,906

DATED : November 10, 1987

INVENTOR(S) : JOHN H. BROPHY and ANTHONY NOCK

It is certified that error appears in the above-identified patent and that said Letters Patent is hereby corrected as shown below:

Col. 4, line 59, correct the spelling of "that".

Col. 5, TABLE 1, line 20, change "(C 63)" to -- (G 63) --.

Signed and Sealed this

Twelfth Day of July, 1988

Attest:

DONALD J. QUIGG

Attesting Officer     Commissioner of Patents and Trademarks